US012600622B2

(12) United States Patent
Alagy et al.

(10) Patent No.: US 12,600,622 B2
(45) Date of Patent: Apr. 14, 2026

(54) SYSTEM AND METHOD FOR STORING AND RE-RELEASING DIHYDROGEN

(71) Applicants: Jacques Alagy, Charbonnieres-les-Bains (FR); Serge Zareh Alagy, Allauch (FR); Annie Alagy, Saint-Didier-Au-Mont-d'Or (FR); Pierre Jean Louis Trambouze, Caluire-et-Cuire (FR)

(72) Inventors: Jacques Alagy, Charbonnieres-les-Bains (FR); Pierre Jean Louis Trambouze, Caluire-et-Cuire (FR)

(73) Assignees: Jacques Alagy, Charbonnieres-les-Bains (FR); Serge Alagy, Allauch (FR); Annie Alagy, Saint-Didier-Au-Mont-D'or (FR); Pierre Trambouze, Caluire-et-Cuire (FR)

( * ) Notice: Subject to any disclaimer, the term of this patent is extended or adjusted under 35 U.S.C. 154(b) by 633 days.

(21) Appl. No.: 17/917,199

(22) PCT Filed: Apr. 6, 2021

(86) PCT No.: PCT/FR2021/050601
§ 371 (c)(1),
(2) Date: Oct. 5, 2022

(87) PCT Pub. No.: WO2021/205113
PCT Pub. Date: Oct. 14, 2021

(65) Prior Publication Data
US 2023/0141528 A1 May 11, 2023

(30) Foreign Application Priority Data

Apr. 6, 2020 (FR) ...................................... 2003405

(51) Int. Cl.
*C01B 3/22* (2006.01)
*C07C 31/20* (2006.01)

(52) U.S. Cl.
CPC ................ *C01B 3/22* (2013.01); *C07C 31/20* (2013.01); *C01B 2203/0277* (2013.01); *C01B 2203/1217* (2013.01)

(58) Field of Classification Search
CPC .............. C01B 3/22; C01B 2203/0277; C01B 2203/1217; C07C 31/20
(Continued)

(56) References Cited

U.S. PATENT DOCUMENTS

2005/0013767 A1* 1/2005 Bagzis .................. C01B 3/0015
423/648.1
2008/0260630 A1 10/2008 Pez et al.

FOREIGN PATENT DOCUMENTS

CN 101189201 A * 8/2008 ............. C01B 3/065
DE 10055717 A1 5/2002
WO 2018163004 A1 9/2018

OTHER PUBLICATIONS

CN 101189201 Machine Translation (Year: 2008).*

* cited by examiner

*Primary Examiner* — Coris Fung
*Assistant Examiner* — Catriona M Corallo
(74) *Attorney, Agent, or Firm* — Nath, Goldberg & Meyer; Joshua B. Goldberg

(57) ABSTRACT

A dihydrogen storage and retrieval method includes at least a step of generating (G) hydrogen by dehydrogenating hydroxyl groups of dipropylene glycol (DG) into respective carbonyl groups in order to produce a dehydrogenated substrate ($S_D$) and gaseous dihydrogen ($H_2$); and, (Continued)

a step of regenerating (R) at least a portion of the dipropylene glycol (DG) by hydrogenating the carbonyl groups into respective hydroxyl groups using the gaseous dihydrogen ($H_2$).

12 Claims, 2 Drawing Sheets

(58) Field of Classification Search
    USPC ....................................................... 423/648.1
    See application file for complete search history.

SYSTEM AND METHOD FOR STORING AND RE-RELEASING DIHYDROGEN

This is a National Phase Application filed under 35 U.S.C. 371 as a national stage of PCT/FR2021/050601, filed Apr. 6, 2021, and claims priority from French Application No. FR2003405, filed Apr. 6, 2020, the content of each of which is hereby incorporated by reference in its entirety.

TECHNICAL FIELD

The present invention relates to the general field of energy carrier storage, and more precisely storage, transportation and recovery of dihydrogen.

More particularly, the invention relates to a dihydrogen storage and retrieval method, as well as a dihydrogen storage and retrieval system. The invention also relates to an integrated assembly comprising the above-mentioned storage and retrieval system.

PRIOR ART

Energy storage and retrieval represent major technical issues imposed to the society since the second industrial revolution, which made widespread use of electricity and internal combustion engine. In particular, production of energy, in particular electricity, has mainly be made from fossil or nuclear sources.

In the same time, there exists a willingness on the part of States to promote new alternatives not only in terms of energy sources but also of energy carriers, in particular as regards energy storage, transportation, and retrieval or recovery, the energy carriers taken on board vehicles being particularly concerned.

There exists today a strong need, for evident ecological reasons of associated significant pollution and economical reasons of ease of storage and redistribution, to find an energy carrier that can be used massively while being clean, that is to say of easy use, little polluting, and allowing an easy storage of any type of energy.

Dihydrogen, commonly called "hydrogen", is contemplated as a high-potential energy carrier suitable for being part of the "energy mix". The latter thus represents the different primary energy sources and by extension the associated energy carriers, such as accumulator batteries or dihydrogen.

The systems and methods for storage, and by extension transportation and recovery, of dihydrogen, although being theoretically satisfying, nevertheless suffer from certain drawbacks.

Indeed, dihydrogen suffers from significant difficulties of exploitation. In particular, the known systems and methods for production, storage, transportation and even recovery of dihydrogen currently involve an extremely heavy and complex implementation, in which the dihydrogen, which exists in gaseous form at ambient temperature, is pressurized at an extremely high pressure, for example 700 bars, or undergoes an extreme cooling, for example −252° C., to be liquefied, such ways to proceed being extremely energy-consuming and very risky for security. Moreover, although the implementation of dihydrogen liquefied by cooling or highly pressurized is known and mastered as such, it requires a dihydrogen storage and/or transportation capacity that is not satisfying as regards the above-mentioned constraints (pressure and/or temperature), which are considerable.

Thus, even if dihydrogen storage and transportation systems and methods are known and realizable as such, the above-mentioned drawbacks demonstrate that they are not adapted to a massive, simple and safety use of dihydrogen as an energy carrier easy to store and transport, as yet required for using the latter in the management of great quantities of energy, for example within the framework of a power plant having to continuously power supply a city or a vehicle propulsion power supply.

Finally, the known systems for the storage, transportation and retrieval of dihydrogen, in particular those based on liquefaction by cooling or on pressurizing, are particularly heavy, bulky, expensive and energy-consuming, and they are moreover highly risky in terms of safety of property and people. They are difficult to adapt on an industrial scale to a regular and easy use of dihydrogen, as well as to the management of storage, transportation and redistribution of great quantities of this energy carrier.

DISCLOSURE OF THE INVENTION

The objects assigned to the present invention therefore aim to remedy the different above-mentioned drawbacks, and to propose a new dihydrogen storage and retrieval method that, while being particularly efficient, is particularly simple to implement, inexpensive and low or even non-polluting.

Another object of the invention aims to propose a new dihydrogen storage and retrieval method whose implementation requires only a limited space, and that does not involve the use of exaggeratedly heavy, bulky, dangerous and/or expensive materials for this storage.

Another object of the invention aims to propose a new dihydrogen storage and retrieval method making it possible to store, transport and finally retrieve dihydrogen in a simple and secure manner, in optimum safety conditions.

Another object of the invention aims to propose a new dihydrogen storage and retrieval method that is particularly easy to adapt to the different sources and uses of dihydrogen.

Another object of the invention aims to propose a new dihydrogen storage and retrieval method that allows the management of high quantities of dihydrogen, and by extension of energy.

Another object of the invention aims to propose a new dihydrogen storage and retrieval method that is both reliable and economically competitive.

Another object of the invention aims to propose a new dihydrogen storage and retrieval method of reduced implementation cost.

Another object of the invention aims to propose a new dihydrogen storage and retrieval method that can be implemented in extreme weather conditions, and in particular extreme cold.

Another object of the invention aims to propose a new dihydrogen storage and retrieval method making it possible to retrieve dihydrogen in a continuous, regular and/or controlled manner over time, from a random, variable and/or sporadic production of dihydrogen.

Another object of the invention aims to propose a new dihydrogen storage and retrieval system that is particularly little polluting, easy to implement and particularly efficient for energy conservation as dihydrogen, including energy generated on an intermittent and/or irregular basis.

Another object of the invention aims to propose a new dihydrogen storage and retrieval system that is particularly wear-resistant and whose efficiency is substantially constant over time, even if it is subjected to prolonged and/or successive uses.

Another object of the invention aims to propose a new dihydrogen storage and retrieval system having an optimized yield, thus allowing the use of the most accurate sizing according to the source of dihydrogen and use thereof.

Another object of the invention aims to propose a new dihydrogen storage and retrieval system that is particularly efficient, adapted and low-bulk for the storage and retrieval of industrial-scale amounts of dihydrogen, and by extension of energy.

Another object of the invention aims to propose a new dihydrogen storage and retrieval system of robust design and that allows the management of high quantities of dihydrogen, and by extension of energy.

Another object of the invention aims to propose a new dihydrogen storage and retrieval method of reduced maintenance cost.

The objects assigned to the invention are achieved by means of a dihydrogen storage and retrieval method comprising at least:

a step of generating hydrogen by dehydrogenating hydroxyl groups of the dipropylene glycol into respective carbonyl groups, in order to generate a dehydrogenated substrate and gaseous dihydrogen, and a step of regenerating at least a portion of the dipropylene glycol, by hydrogenating said carbonyl groups into respective hydroxyl groups by means of gaseous dihydrogen.

The objects assigned to the invention are also achieved by means of a dihydrogen storage and retrieval system comprising at least:

a module for generating hydrogen designed to dehydrogenate hydroxyl groups of dipropylene glycol into respective carbonyl groups, in order to generate a dehydrogenated substrate and gaseous dihydrogen, and a module for regenerating at least a portion of the dipropylene glycol, designed to hydrogenate said carbonyl groups into respective hydroxyl groups by means of gaseous dihydrogen.

The objects assigned to the invention are moreover achieved by means of an integrated assembly comprising the above-described dihydrogen storage and retrieval system, and a motor vehicle whose propulsion requires dihydrogen, the hydrogen generation module of the storage and retrieval system being taken on board the motor vehicle to provide the latter with at least a portion of the dihydrogen required for its propulsion.

BRIEF DESCRIPTION OF THE DRAWINGS

Other features and advantages of the invention will appear in more detail upon reading of the following description, with reference to the appended drawings, given by way of purely illustrative and non-limiting examples, in which.

BEST WAY TO IMPLEMENT THE INVENTION

Figure 1:
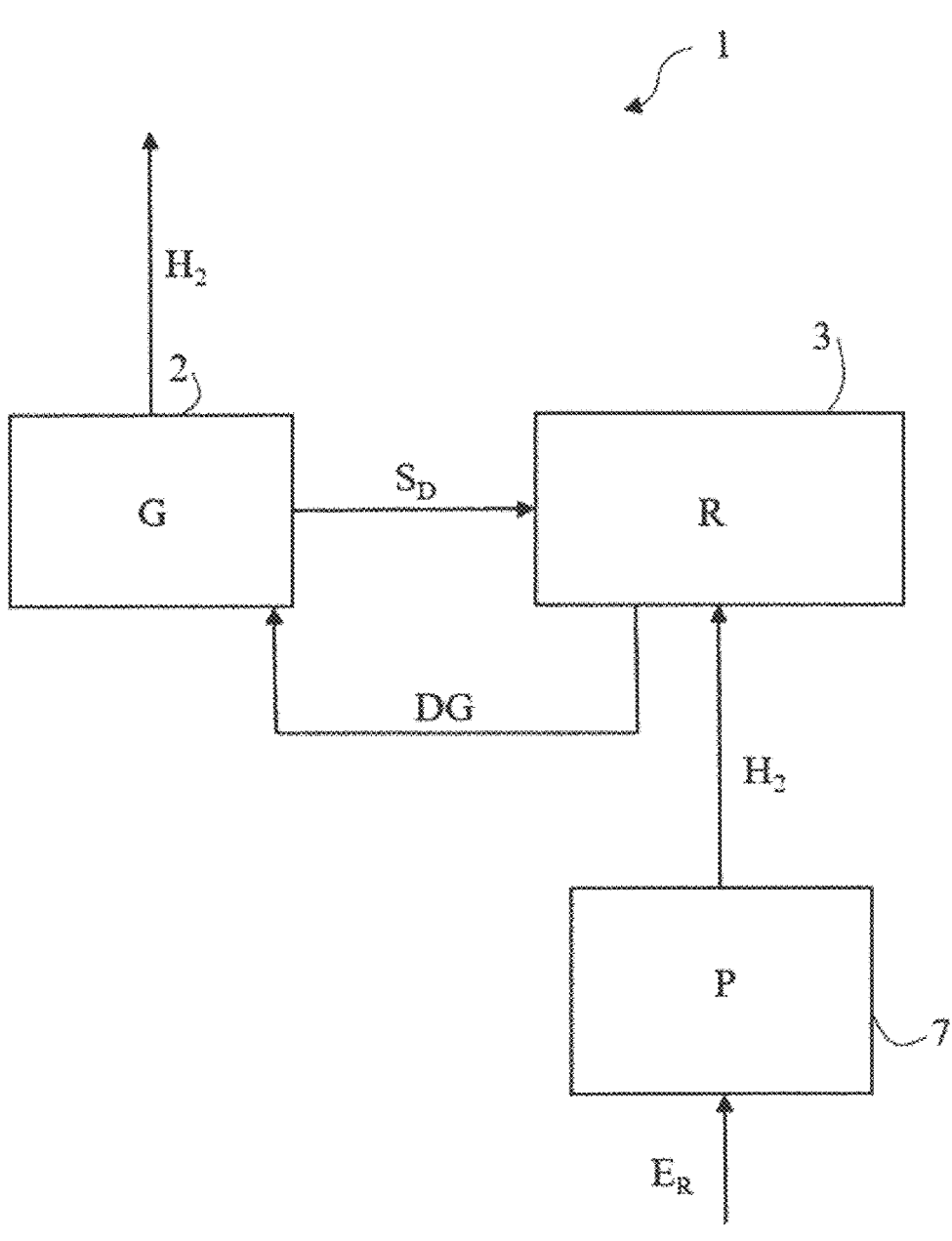
FIG. 1 is a simplified schematic illustration of a dihydrogen storage and retrieval method of the invention, and an associated system.

As illustrated in the figures, the invention relates, according to a first aspect, to a dihydrogen storage and retrieval method. The invention also relates as such, according to a second aspect, also illustrated in the figures, to a dihydrogen storage and retrieval system 1, preferably designed to operate according to the dihydrogen storage and retrieval method mentioned hereinabove and described in more detail hereinafter. Preferentially, the following description relating to the dihydrogen storage and retrieval system 1 also applied to the dihydrogen storage and retrieval method according to the invention, and conversely.

According to the invention, the dihydrogen storage and retrieval method comprises at least one step of generating hydrogen G by dehydrogenating hydroxyl groups of the dipropylene glycol DG into respective carbonyl groups, in order to generate a dehydrogenated substrate $S_D$ and gaseous dihydrogen $H_2$. Therefore, according a second aspect of the invention, the dihydrogen storage and retrieval system 1 comprises at least one hydrogen generation module 2 designed to dehydrogenate hydroxyl groups of dipropylene glycol into respective carbonyl groups, in order to generate a dehydrogenated substrate $S_D$ and gaseous dihydrogen $H_2$. Obviously, the generation step G is preferentially carried out within said generation module 2. The above-mentioned dehydrogenation is advantageously to be understood as a chemical dehydrogenation reaction, which is potentially catalytic, as will be seen hereinafter. The phrase "generation of hydrogen" can obviously be understood as meaning "generation of dihydrogen".

According to the invention, the method further comprises a step of regenerating R at least a portion of the dipropylene glycol DG, by hydrogenating said carbonyl groups into respective hydroxyl groups by means of gaseous dihydrogen $H_2$. Thus, according to a second aspect of the invention, the dihydrogen storage and retrieval system further comprises a module 3 for regenerating at least a portion of the dipropylene glycol DG.

Said regeneration module 3 is designed to hydrogenate said carbonyl groups into respective hydroxyl groups by means of gaseous dihydrogen $H_2$. Obviously, the regeneration step R is preferentially carried out within said regeneration module 3. The above-mentioned hydrogenation is advantageously to be understood as a chemical hydrogenation reaction, which is potentially catalytic, as will be seen hereinafter.

The invention allows in particular avoiding the need to store and transport dihydrogen $H_2$ alone, this gas being difficult and even dangerous to handle, store and transport at ambient temperature. Usually, in common uses of dihydrogen, the storage and transportation of this compound is made:

in liquid form, by cryogeny, which is as such rather expensive in cooling energy: it is necessary to lower the temperature of the dihydrogen $H_2$ down to about −252° C.; it is then possible to store 6.66 kg of dihydrogen $H_2$ in a volume of 100 L (cryogenic container); or in gaseous form, at high pressure generally between 300 and 700 bars; it is then possible in these conditions to store up to 4 kg of dihydrogen $H_2$ in a volume of 100 L.

The last two methods for the storage of dihydrogen $H_2$, cryogeny (liquid dihydrogen) and pressurizing (gaseous dihydrogen), both have evident drawbacks including the cost, in particular in energy, and the risks associated with their handling and storage, which thus require specific infrastructures and vehicles to store, transport and distribute the cooled liquid or pressurize gaseous dihydrogen, for example heavy cooling means, a very high insulation refrigerated container, cylinders supporting very high pressures, complex pressurized storage means, etc. The cooled liquid dihydrogen, for example, is used in particular as fuel for spatial shuttle launch, but its massive use remains of course very difficult to implement given the physical constraints imposed (very low temperature, cryogenic container, risks related to safety of property and people and associated protection means, energy expense for the cooling, etc.). The system 1 and the method of the invention thus allow storing dihydrogen $H_2$ in chemical form in a completely efficient and competitive manner with regard to the storage capacities compared to those of dihydrogen cryogeny or pressurizing.

The invention advantageously makes it possible to store and possibly transport dihydrogen $H_2$ in stable chemical form (liquid), that is to say as dipropylene glycol DG (and more precisely hydroxyl groups of the latter), waiting for the dihydrogen $H_2$ to be generated in gaseous form during said generation step G, to then be used, for example, in the engine of a vehicle or the turbine of a power plant, as will be seen hereinafter. Indeed, the dipropylene glycol DG can not only be easily stored and transported in liquid form at ambient temperature and atmospheric pressure, but it further consti-tutes a non-aggressive and low-irritant product of very low toxicity, and is almost odourless, thus allowing a low-constraint conservation (and possible transportation) of the dihydrogen $H_2$, the latter being virtually contained "within" the dipropylene glycol DG that essentially serves as a stable liquid support thereto. Moreover, the dipropylene glycol DG is very little polluting and, as such, presents a very low risk for the environment, even in case of accidental release of this compound. Dipropylene glycol DG further has boiling and melting points that make it extremely easy to store and to transport in a wide variety of ambient temperature con-ditions (external in particular), especially extreme cold or extreme heat, without risk of freezing for example. For example, at atmospheric pressure, the boiling point of the dipropylene glycol DG is about 230° C. (+/−3° C.), whereas its melting point is about −39° C. (+/−2° C.), a slight variation being possible (but possibly greater than that mentioned) according to the distribution of the isomers and the purity of the product. In other words, the system 1 and the method of the invention allow using in an advantageous manner the dihydrogen $H_2$ as an energy carrier in the form of dipropylene glycol DG.

Moreover, the dipropylene glycol DG implemented within the framework of the invention is advantageously a product sold in great quantities, that can be found particu-larly easily at competitive and thus controlled costs. The dipropylene glycol DG is preferably formed by a mixture of the following isomers: 1,1'-oxydi-2-propanol, 2-(2-hydroxy-propoxy)-1-propanol, and 2,2'-oxydi-1-propanol. Such a mixture of three isomers typically represents dipropylene glycol DG that is commonly found in stores. The dipropyl-ene glycol DG thus advantageously results from a reaction between propane-1,2-diol (also called propylene glycol) and 1,2-epoxypropane (also called methyloxirane), during a syn-thesis step being potentially part of said method.

Figure 2:
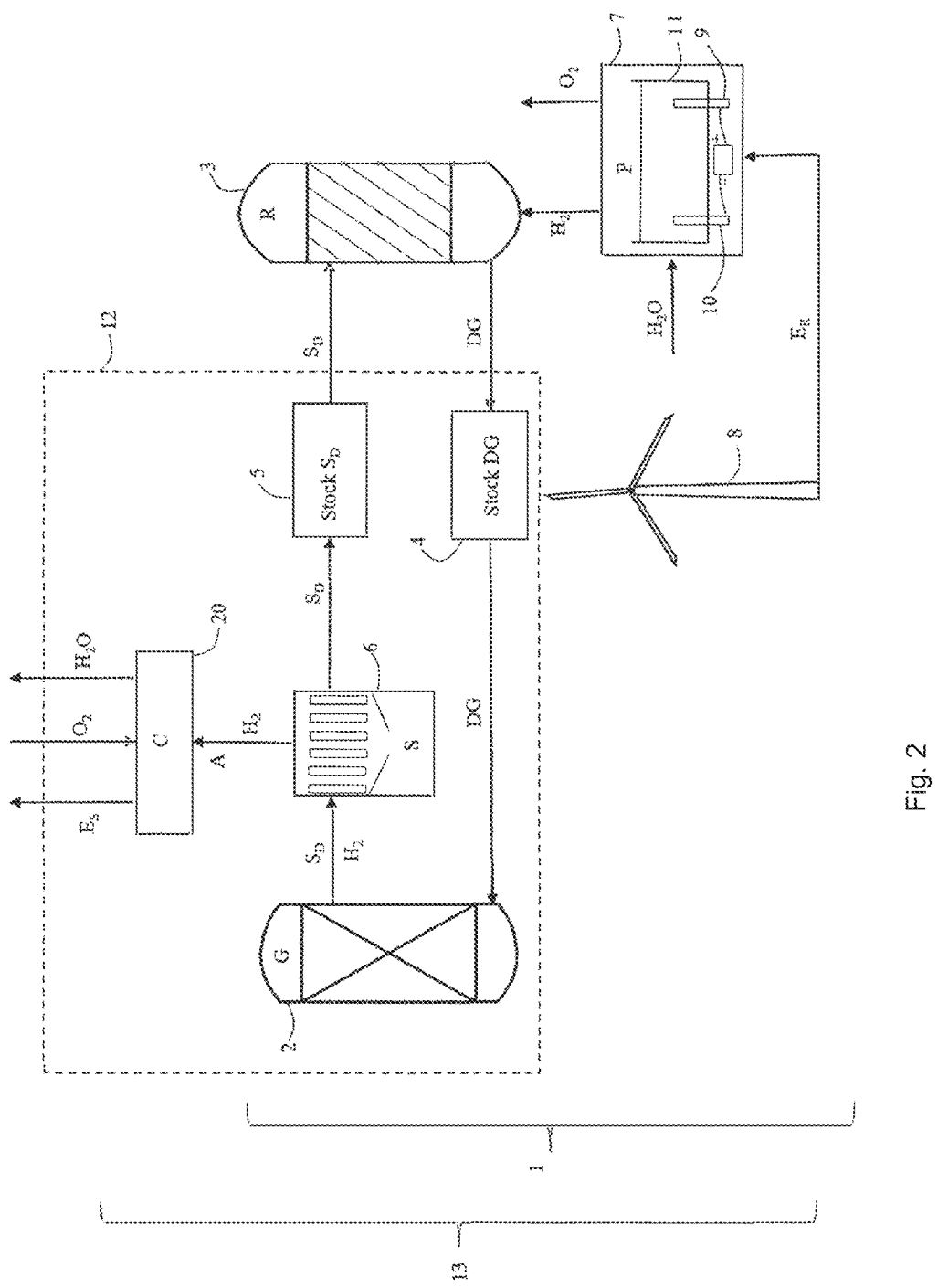
FIG. 2 is a detailed schematic illustration of an exemplary dihydrogen storage and retrieval system of the invention, and an associated method, compatible with system and method of FIG. 1.

Advantageously, as illustrated in FIG. 2, the system 1 comprises a first storage means 4 designed to store the dipropylene glycol DG intended to be consumed during said generation step G, within the generation module 2. Advan-tageously, the system 1 moreover comprises a second stor-age means 5 designed to store the dehydrogenated substrate $S_D$ coming from the generation module 2, and intended to be consumed during said regeneration step R, within the regen-eration module 3. Obviously, the first storage means 4 is moreover preferably designed to store the dipropylene gly-col DG regenerated during said regeneration step R, within the regeneration module 3. Such a configuration makes it possible to have "buffer" stocks of said dehydrogenated substrate $S_D$ and said dipropylene glycol DG.

According to a first embodiment, said hydroxyl groups are of the secondary alcohol type, and said carbonyl groups are of the ketone type. Advantageously, the ketone-type carbonyl groups of the dehydrogenated substrate $S_D$ are obtained from the dehydrogenation at least of the two secondary alcohol-type hydroxyl groups of the 1,1'-oxydi-2-propanol and the 2-(2-hydroxypropoxy)-1-propanol (which has only one of them), the 2,2'-oxydi-1-propanol having no secondary alcohol-type hydroxyl group, and only two primary alcohol-type hydroxyl groups.

Preferably, the 1,1'-oxydi-2-propanol is the dominant iso-mer of the dipropylene glycol DG, and constitutes prefer-ably at least 40% in weight of the dipropylene glycol DG, more preferentially at least 60% in weight of the dipropylene glycol DG, still more preferentially at least 80% in weight of the dipropylene glycol DG, the other isomers forming the almost-totality or the totality of the rest. Particularly advan-tageously, during said hydrogen generation step G, prefer-ably within said generation module 2, the dipropylene glycol main isomer, the 1,1'-oxydi-2-propanol, sees its two hydroxyl groups be dehydrogenated into two respective carbonyl groups. Each molecule of 1,1'-oxydi-2-propanol thus advantageously undergoes a dehydrogenation in such a way as to provide two molecules of dihydrogen. The 1,1'-oxydi-2-propanol is thus preferably dehydrogenated into 1,1'-oxydiacetone (also called 1,1'-oxybis(propan-2-one), or also 1-(2-oxo-propoxy)-propan-2-one). Thus, preferentially, during said step of regenerating R the dipropylene glycol DG, preferably within said regeneration module 3, the dehydrogenated substrate $S_D$ sees its two ketone-type car-bonyl groups be hydrogenated into two respective secondary alcohol-type hydroxyl groups. The whole energy expense, for such a dehydrogenation of the 1,1'-oxydi-2-propanol into 1,1'-oxydiacetone (and more generally into dehydrogenated substrate $S_D$) by the generation module 2 during the gen-eration step G, and for such a hydrogenation of the 1,1'-oxydiacetone into 1,1'-oxydi-2-propanol by the regeneration module 3 during the regeneration step R, is relatively low.

According to a particular alternative of the first embodi-ment mentioned hereinabove, said hydroxyl groups are only of the secondary alcohol type, and said carbonyl groups are only of the ketone type. In other words, according to this alternative, during the generation step G, within the genera-tion module 2, the only hydroxyl groups to be dehydroge-nated into respective carbonyl groups are of the secondary (and not primary) alcohol type, and during the generation step G, within the generation module 2, the only carbonyl groups to be dehydrogenated into respective hydroxyl groups are of the ketone (and not aldehyde) type.

Therefore, according to a first particular embodiment, during said hydrogen generation step G, preferably within the generation module 2, the 2-(2-hydroxypropoxy)-1-pro-panol isomer of the dipropylene glycol DG sees (only) its secondary alcohol-type hydroxyl group be dehydrogenated into a ketone-type carbonyl group, whereas its primary alcohol-type hydroxyl group does not react.

According to a second embodiment, during said genera-tion step G, preferably within the generation module 2, all the hydroxyl groups of the different isomers of the dipro-pylene glycol DG are dehydrogenated into respective car-boxyl groups. In this case, during said regeneration step R, preferably within the regeneration module 3, the ketone-type carbonyl groups are advantageously the only groups to be hydrogenated into hydroxyl groups (which are thus of the secondary alcohol type), whereas their aldehyde-type carbonyl groups, if present, do not react. In other words, only the 1,1'-oxydi-2-propanol isomer is advantageously (entirely) regenerated.

According for example to the first embodiment described hereinabove, the 2-(2-hydroxypropoxy)-1-propanol isomer is dehydrogenated for example into the 2-(2-hydroxypropoxy)-propanone isomer. More generally, the 2-(2-hydroxypropoxy)-1-propanol isomer is dehydrogenated for example into a conjugated compound partially dehydrogenated with a ketone-type carbonyl group and a primary (thus non-dehydrogenated) alcohol-type hydroxyl group. During said regeneration step R, the secondary alcohol-type hydroxyl group is regenerated and the 2-(2-hydroxypropoxy)-1-propanol isomer is thus reconstituted. According for example to the second embodiment described hereinabove, the 2-(2-hydroxypropoxy)-1-propanol isomer sees its two hydroxyl groups be dehydrogenated into two respective carbonyl groups, one of the ketone type and the other of the aldehyde type, during the generation step G, within the generation module 2, then only said ketone-type carbonyl group is regenerated (hydrogenated) into a secondary alcohol-type hydroxyl group during said regeneration step R, within the regeneration module 3.

Preferably, during said hydrogen generation step, preferentially within the generation module 2, the 2,2'-oxydi-1-propanol isomer of the dipropylene glycol does not react (in other words, its two aldehyde-type carbonyl groups are not hydrogenated into primary alcohol-type hydroxyl groups).

According to a particular embodiment, the dihydrogen storage and retrieval method comprises, after said hydrogen generation step G and before said regeneration step R, a step (not illustrated) of dividing the dehydrogenated substrate $S_D$ into several fractions, each fraction of dehydrogenated substrate resulting from the dehydrogenation or the non-dehydrogenation of a different respective isomer of the dipropylene glycol during said generation step G. Therefore, the system 1 advantageously comprises, according to this particular embodiment, means for dividing (i.e. separating) the dehydrogenated substrate $S_D$ into several fractions, each resulting from the dehydrogenation or the non-dehydrogenation of a different respective isomer of the dipropylene glycol DG. These division means comprise for example a fractional distillation column. For example, according to an already-mentioned embodiment, the 1,1'-oxydi-2-propanol, Ie 2-(2-hydroxypropoxy)-1-propanol, and the 2,2'-oxydi-1-propanol are each dehydrogenated at different respective levels during said generation step G, the 1,1'-oxydi-2-propanol seeing its two carbonyl groups (of the ketone type) be dehydrogenated into two hydroxyl groups (of the secondary alcohol type), the 2-(2-hydroxypropoxy)-1-propanol seeing only one hydroxyl group (of the secondary alcohol type) be dehydrogenated into a carbonyl group (of the ketone type), whereas its other hydroxyl group (of the primary alcohol type) is not dehydrogenated into a carbonyl group (that would be of aldehyde type), the 2-(2-hydroxypropoxy)-1-propanol thus keeping a single hydroxyl group (of the primary and non-secondary alcohol type), and the 2,2'-oxydi-1-propanol having none of its hydroxyl groups dehydrogenated. The different fractions may be separated in particular thanks to their different respective boiling points. The fraction resulting from one or several of the less dehydrogenated and/or non-dehydrogenated isomers can then be transferred, to another location than in the regeneration module 3, that is to say they do not undergo the regeneration step R, in such a way that, during said regeneration step R, within said regeneration module 3, the dehydrogenated substrate $S_D$ that is regenerated is mainly composed of the isomer resulting from the isomer the most dehydrogenated during said generation step G, i.e. advantageously, the 1,1'-oxydi-2-propanol (dehydrogenated into oxydiacetone). It is hence perfectly possible that the dipropylene glycol DG initially used undergoes in a way a "purification" after having been dehydrogenated then regenerated, in such a way as to keep the isomer(s) that is (are) the most efficient in the storage of the dihydrogen $H_2$, that is to say the isomer(s) that are the most dehydrogenated during said generation step G. There thus can be a difference between the dipropylene glycol DG that is initially used to undergo a first dehydrogenation during a first generation step G, and that preferably contains a mixture of isomers, and that which is generated by hydrogenation during the regeneration step R, and that contains in almost-totality a single isomer (or as an alternative almost only two isomers). The division step can be particularly advantageous to keep the isomer(s) of the dipropylene glycol DG that are the most efficient for the "chemical storage" of dihydrogen $H_2$ while recovering the other isomers, potentially reusable for example as polymers.

As an alternative, during said generation step G, preferably within the generation module 2, all the hydroxyl groups of the different isomers of the dipropylene glycol DG, whether they are of the primary or secondary alcohol type, are dehydrogenated into ketone or aldehyde, that is to say that they are dehydrogenated into respective carbonyl groups (aldehyde for the primary alcohol and ketone for the secondary alcohol).

For example, during said generation step G, within the generation module 2, the dehydrogenation is carried out at a temperature between 120° C. and 300° C., preferably between 160° C. and 260° C., either at atmospheric pressure, or at a pressure between 1 and 5 bars, or between 5 and 10 bars. Preferentially, the dipropylene glycol DG has a boiling temperature substantially higher than that of the dehydrogenated substrate $S_D$, and will be able to more easily escape, with the so-formed dihydrogen $H_2$, from the generation module 2 of dehydrogenation 10, during the generation step G. The generation module 2 advantageously comprises all the equipment suitable for making such a dehydrogenation (in particular catalytic), for example at least a dehydrogenation reactor, a heating means, a purification means and/or means for separating the compounds at the reaction exit/end, a means for collecting and evacuating the dehydrogenated substrate $S_D$, etc. Generally, the generation module 2 preferably has at its inlet the dipropylene glycol DG in liquid state (coming directly from the regeneration module 3 or via the first storage means 4, for example), and at its outlet the so-formed dehydrogenated substrate $S_D$, preferably in gaseous state, and the generated dihydrogen H2, at the gaseous state. Advantageously, the dehydrogenation of the generation step G is carried out in softer conditions than the hydrogenation of the regeneration step R, for example under atmospheric pressure or slightly higher, for example between 2 and 5 bars inside said generation module 2.

Preferably, the system 1 further comprises means for separating the dehydrogenated substrate $S_D$ and the dihydrogen $H_2$ that have been generated within said generation module 2. Thus, the method advantageously comprises a step of separating S the dehydrogenated substrate $S_D$ and the dihydrogen $H_2$ that have been generated during said generation step G. For example, said separation means comprise at least one cooling unit 6, in such a way that, during said separation step S, the gaseous dihydrogen $H_2$ and the dihydrogen $S_D$ generated by said generation module 2 (preferably both at the gaseous state) are separated from each other, the dehydrogenated substrate $S_D$ being thus condensed by cooling to become liquid whereas the dihydrogen $H_2$ remains gaseous.

For example, during said regeneration step R, within the regeneration module 3, the hydrogenation is carried out at a temperature between 100 and 280° C., preferably between 120° C. and 260° C., more preferentially between 140° C. and 240° C., at a pressure advantageously between 5 and 150 bars, more advantageously between 10 and 90 bars.

According to an example compatible with the above, during the regeneration step R, within said regeneration module 3, the hydrogenation is carried out continuously with fixed-bed catalysts, and according to a triphasic regime with downward co-current.

According to an advantageous embodiment of the invention, the generation and regeneration steps are carried out by means of one or several catalysts, preferably metallic, for example nickel- and/or ruthenium-based. Therefore, advantageously, the generation step includes a catalytic dehydrogenation of the dipropylene glycol DG, whereas the regeneration step includes a catalytic hydrogenation of the dehydrogenated substrate $S_D$. Said generation 2 and regeneration 3 modules thus preferably contain one or several catalysts, in particular metallic, for example nickel- and/or ruthenium-based. Very different catalysts may be used, both during dehydrogenation and hydrogenation, including those which are nickel- and ruthenium-based, deposited on a charcoal support, these catalysts having optionally been doped with very low quantities of platinum (lower than 0.2% in weight, in particular) to improve their activity. The selectivity of the hydrogenation reaction is preferentially very high, and in particular higher than 99%. The catalytic dehydrogenation advantageously comprises an oxidation reaction of the dipropylene glycol DG, whereas the catalytic hydrogenation preferably comprises a reduction reaction by the dihydrogen $H_2$ of the dehydrogenated substrate $S_D$. The catalytic dehydrogenation can be written DG+catalyst→$S_D$+$H_2$+catalyst, and the catalytic hydrogenation can be written $S_D$+$H_2$+catalyst→DG+catalyst.

Advantageously, during said hydrogen generation step G, preferably within the generation module 2, the dehydrogenated substrate $S_D$ is also at the gaseous state. More advantageously, during the generation step G, the dehydrogenated substrate $S_D$, in gaseous form, is evacuated as the dehydrogenation progresses, at the same time as the gaseous dihydrogen $H_2$. Said hydrogen generation module 2 is thus preferentially designed to evacuate the dehydrogenated substrate $S_D$ (resulting from the dipropylene glycol DG, and/or from a regenerated fraction of dipropylene glycol), in gaseous form, as the dehydrogenation progresses, at the same time as the dihydrogen $H_2$ (which hence results from the dehydrogenation of the dipropylene glycol DG or from a regenerated fraction of dipropylene glycol), also in gaseous form. Such a configuration allows in particular to improve the progress and/or the speed of the dehydrogenation.

Advantageously, during said generation step G, within generation module 2, the dihydrogen $H_2$ generated on the one hand, and the dehydrogenated substrate $S_D$ generated on the other hand, leave by evaporation the liquid reactional medium both to move the reaction equilibrium and to avoid the inhibitor effect of potential ketone functions of the dehydrogenated substrate $S_D$ on the catalyst.

According to a particular embodiment, said method and said system 1 are intended to allow the management of dihydrogen formed using renewable energy (or any other source) resulting for example from an intermittent and/or irregular production, which is of course also valuable for the storage and retrieval method of the invention. Indeed, for evident economical reasons of shortage risks and ecological reasons linked to the pollution, in particular with carbon, researches are currently made to replace at least part of the so-called "non-renewable" sources of energy by so-called "renewable" sources of energy, that is to say which are renewed relatively rapidly at human scale by the nature, and whose exploitation is moreover less polluting, but often intermittent and/or irregular. Therefore, the system 1 and the method of the invention are suitable for the management, i.e. in particular the storage and transportation, of dihydrogen formed by means of any type of energy, and in particular renewable energy.

Therefore, the method comprises for example a step of producing P dihydrogen $H_2$ at the gaseous state, using renewable energy $E_r$, in order for this produced hydrogen $H_2$ to be used during said regeneration step R. Preferably, the dihydrogen storage and retrieval system 1 comprises a module for producing 7 dihydrogen $H_2$ at the gaseous state, designed to operate using renewable energy $E_r$ and to supply said regeneration module 3 with dihydrogen $H_2$. For example, the renewable energy $E_r$ is of intermittent production type (that is to say a production that may sometimes be null) and/or irregular production type (that is to say a production that varies generally significantly over time), such as solar or wind energy, or also such as geothermal or hydraulic energy, and in particular hydroelectric energies such as tidal, marine current, osmotic and wave energies. The system 1 and the method are hence, according to this last example, designed to be implemented thanks to said renewable energy $E_r$, which is for example generated in electric, thermal and/or mechanical form, and has an irregular, variable, or even discontinuous or intermittent nature over time. As an alternative, said renewable energy $E_r$ may also be of the regular and/or controlled production type, such as the energy resulting from the biomass. According to a particular example, the system 1 of the invention comprises as such a renewable energy generation unit of intermediate and/or irregular production 8, said unit 8 being designed to supply at least said production module 7 (and possibly said generation 2 and regeneration 3 modules) with renewable energy $E_r$. Said unit 8 comprises for example one or several wind turbines 8, as illustrated in FIG. 2. Said renewable energy $E_r$ is thus, according to an advantageous alternative resulting from an energy of intermittent and/or irregular production, such as solar energy (of thermal, thermodynamic or photovoltaic origin, in particular) or wind energy (of mechanical origin, in particular).

Therefore, the method and system 1 of the invention allow both the easy accumulation of dihydrogen (in stable, liquid form, chemically transformed: the dipropylene glycol DG), in particular regenerated using said renewable energy $E_r$, and the generation of said dihydrogen $H_2$ when its consumption is required to supply for example the power grid, but also for example a vehicle such as truck (heavy truck), car, train, ship, etc. or any other structure requiring an energy supply (in particular, electricity but not only) to operate, for example charging stations for hydrogen cars. Therefore, the generation 2 and regeneration 3 modules are advantageously directly linked to each other to generate, as soon as there is a peak of production and/or a dip of consumption of renewable energy of intermittent and/or irregular production, dihydrogen $H_2$ "stored" in a stable manner as dipropylene glycol DG, regenerated from a dehydrogenated substrate $S_D$. The so-regenerated dipropylene glycol DG can then be potentially safely transferred or transported up to the generation module 2 within which it will be dehydrogenated to allow the retrieval of the dihydrogen $H_2$ in gaseous form, when this energy needs to be consumed (for example as soon as there is a dip of production and/or a peak of consumption of renewable energy of intermittent and/or irregular production). The system 1 and the method of the invention thus advantageously allows storing, transporting and redistributing in simple, efficient and easy way the dihydrogen $H_2$ produced by means of renewable energies in stable liquid form, said stable liquid being in particular the dipropylene glycol DG, which may be regenerated indefinitely from the hydrogenation of the dehydrogenated substrate $S_D$, as many times as required, with very few loss on the system 1, thus forming a chemical cycle whose only global inputs and outputs are the dihydrogen $H_2$ and above all the energy from renewable sources (as well as potentially a fraction of dehydrogenated substrate $S_D$ resulting from a slight hydrogenation or a non-hydrogenation of one or several of the isomers of the dipropylene glycol DG). The general ideal of the invention is thus to transform the dipropylene glycol DG into dehydrogenated substrate $S_D$ and dihydrogen $H_2$ in order to use the latter as a clean energy carrier, then to regenerate the dipropylene glycol DG, in particular using a renewable energy $E_r$ of substantially intermittent and/or irregular production (but not necessarily). Such a configuration allows an easier accumulation of the dipropylene glycol DG in any circumstances, whether the production of energy (and by extension of dihydrogen) is regular or not, and that in an easy and safe manner, because the dipropylene glycol DG is easy to store, at the liquid state, at ambient temperature and atmospheric pressure. Thanks to the invention, the dihydrogen $H_2$ (and by extension the energy) that is not immediately consumed is advantageously "chemically stored" as dipropylene glycol DG.

For example, said production step P comprises an electrolyse of water, during which the following reaction occurs: $2H_2O \rightarrow 2H_2 + O_2$. Therefore, the generation module 2 is preferably equipped so that an electrolyse of water, that is to say a decomposition of liquid water into gaseous dihydrogen $H_2$ and dioxygen $O_2$, as described hereinabove, can be carried out therein. The production module 7 advantageously comprises, in particular, in a manner known per se, an anode 9, a cathode 10, at least one electrolyte (for example sodium sulphate) and a vessel 11 in which are placed said electrolyte, anode 9 and cathode 10 (partially for the last two ones), and water. In this embodiment, the wind turbine 8 illustrated in FIG. 2 supplies the production module 7 with electricity to carry out the electrolyse of water. During the electrolyse of water, the dioxygen $O_2$ and the dihydrogen $H_2$ are advantageously separated from each other without particular effort, dioxygen $O_2$ being formed and evacuated at the anode 9 whereas the dihydrogen $H_2$ is formed and evacuated at the cathode 10. The above-mentioned electrolyse of water allows in particular generating dihydrogen $H_2$ from an electric energy, and within the framework of the invention, from electricity preferably coming from a renewable source of energy $E_r$. According to another example of the electrolyse, the dihydrogen $H_2$ is generated within the production module 7, during the step of production P, by gasification of the biomass. This makes it possible to generate mainly dihydrogen $H_2$ without emission of carbon gas of fossil origin. It is then advantageously talked about carbon-free energy carrier from a fossil point of view, which therefore does not impact the greenhouse effect. As an alternative, the dihydrogen $H_2$ is generated within the production module 7, during the production step P, by means of a methane steam cracking reaction, as a co-product of the carbon dioxide.

The system 1 and the method of the invention are particularly suitable to be implemented at the time of peaks of energy production (preferably renewable energy) and/or dips of consumption of a potential power grid, in order to store the dihydrogen $H_2$ generated thanks to the excess energy. In particular, the management of certain high-potential renewable energies for example solar energy (in particular photovoltaic or thermal), wind energy, or even hydraulic energy, is made difficult due to the intermittent and/or irregular nature of their production or yield, with production peaks and dips often difficult to predict, as it is the case in particular for wind energy, whose yields significantly vary as a function of the weather conditions. Therefore, the renewable energy production, in electrical or mechanical form, is uneven and difficult to predict over time, and thus generally does not correspond to the instantaneous needs, for example those of a power grid having to be power supplied thereby. There thus exists a significant need to store the renewable energies without consuming them immediately, that is to say to store them for later use. Indeed, certain so-called renewable energies do not follow the same rhythm as the instantaneous consumption, i.e. the quantity of energy required at a given instant to supply for example a power plant, a production unit or a power grid, having consumption peaks and dips. A contrario, certain renewable energies such as biomass have not the same irregular and/or intermittent nature, and can require to be accumulated and redistributed at will, advantageously by means of an energy carrier such as the dihydrogen $H_2$, as provided by the invention. Today, in particular during the peaks of production of renewable energy, the storage of the energy that is not consumed immediately is generally made as electricity by means of accumulator batteries. These latter tend to be degraded at each use, to lose charging efficiency over time, even without frequent use, due to battery ageing, to be self-discharged over time, and their manufacturing and potential recycling, recovery or discarding are particularly complex, expensive and polluting, in particular compared to the quantity of electric energy that can be stored therein. These batteries, because of the irregularities, at a given instant, of production and consumption of the renewable energies, are constantly solicited to store or retrieve said energies as electricity, which causes their extremely rapid wearing. Thus, the above-mentioned drawbacks demonstrate that these batteries do not suit, as an energy carrier, for a massive and repeated use over time, as yet required for example for supplying motor vehicles or a power plant grid. The electric accumulator batteries are moreover particularly expensive and polluting. They wear out easily and see their performances be degraded over time, in particular if they are subjected to a repeated and/or prolonged use. Such batteries are hence difficult to adapt industrially to the management of the storage and redistribution of great quantities of energy, moreover produced and consumed in an irregular, intermittent and/or unpredictable way. Thus, the dihydrogen storage and retrieval system 1 and the method of the invention make it possible to answer advantageously to the double problem of the storage, transportation and recovery (or retrieval) of the dihydrogen as an energy carrier, on the one hand, and (optionally) the management of the renewable energies of any type, such as energy resulting from the biomass, and even of the intermittent and/or irregular production type, such as wind energy and solar energy, on the other hand.

The method and system 1 of the invention hence make it possible in particular to "smooth", that is to say to make stable and/or controllable over time, a considered production of energy, advantageously renewable and of intermittent and/or irregular production, and that, thanks to the formation of a "buffer" stock of dihydrogen $H_2$ in stable liquid form (dipropylene glycol DG), its timely consumption (thus providing the dehydrogenated substrate $S_D$), and the regeneration thereof (as regenerated dipropylene glycol DG).

The system 1 and in particular the generation module 2 can also be adapted to consume another type of energy, for example an energy of fossil or nuclear source, but it finds its most advantageous application in the application to renewable energy $E_r$, in particular (but not only) of intermittent and/or irregular production, as exposed hereinabove. To sum up, the energy making it possible to generate the dihydrogen $H_2$ is for example of the renewable type (of intermittent/irregular production, such as wind energy, or not, such as biomass), nuclear or fossil (the energy $E_r$ can also more generally refers to "the inbound energy" $E_r$ used by the system 1 and the method of the invention).

Preferably, the system 1 further comprises a consumption module 20 within which the generated dihydrogen $H_2$ coming from the generation module 2 is consumed in such a way as to provide energy in mechanical and/or electrical form, for example in such a way as to retrieve at least in part said renewable energy $E_r$ in the form of an outbound mechanical and/or electrical energy $E_s$. Thus, the dihydrogen storage and retrieval method further advantageously comprises a step of consuming C dihydrogen $H_2$ formed during said generation step 2 in order to provide energy in mechanical and/or electrical form, for example in such a way as to retrieve at least in part said renewable energy $E_r$ in the form of mechanical and/or electrical energy. Advantageously, said steps G, C, P, R are hence carried out successively in order to form a cycle of energy storage in chemical form and redistribution of energy in a mechanical and/or electrical form.

On a vehicle, it is for example possible to generate dihydrogen $H_2$ by means of mini-generators making the dehydrogenation of the dipropylene glycol DG in order to supply a hydrogen fuel cell of said vehicle with dihydrogen $H_2$. Thus, according to a particular embodiment, the dihydrogen storage and retrieval method comprises a supply step A, during which dihydrogen $H_2$ generated during said generation step G, is supplied to a motor vehicle 12 to ensure the propulsion of the latter.

According to a third aspect illustrated in FIG. 2, the invention also relates as such to an integrated assembly 13 comprising the dihydrogen storage and retrieval system 1 as described hereinabove and a motor vehicle 12 whose propulsion requires dihydrogen $H_2$. Preferentially, the above description relating to the system 1 and the method also applies to the integrated assembly 13 as regards their common elements, and conversely.

According to the third aspect of the invention, the hydrogen generation module 2 of the storage and retrieval system 1 is taken on board the motor vehicle 12 to provide the latter with at least a portion of the dihydrogen $H_2$ required for its propulsion. Thus, the vehicle 12 advantageously comprises a propulsion means requiring dihydrogen $H_2$ to operate, such as a fuel cell. The dihydrogen consumption module 20 is thus here preferentially formed by said propulsion means, and the outbound energy $E_s$ is advantageously the mechanical energy propelling said vehicle 12.

Preferably, the dipropylene glycol DG to be dehydrogenated by said hydrogen generation module 2 is taken on board said vehicle 12, for example within said first storage means 4. The dehydrogenated substrate $S_D$ can also be taken on board said vehicle 12, for example within said second storage means 5. That way, the vehicle 12 of the integrated assembly 13 advantageously takes on board at least:

the hydrogen generation module 2;

the separation means, and in particular said cooling unit 6;

the first and second storage means 4, 5.

The integrated assembly 13 preferentially comprises a charging station, designed to collect the dehydrogenated substrate $S_D$ coming from said vehicle 12, to store the dipropylene glycol DG regenerated by the regeneration module 3 of the storage and retrieval system 1, and to supply said motor vehicle 12 with regenerated dipropylene glycol DG. Said charging station can potentially comprise the regeneration module 3 and moreover preferably comprises a third storage means for storing regenerated dipropylene glycol DG.

The implementation of dipropylene glycol, and in particular 1,1'-oxydi-2-propanol, is particularly advantageous due, inter alia, to its two secondary alcohol groups, its relatively low density, its high ebullition point (about 230° C.) that makes it possible to obtain a high reaction speed (for the dehydrogenation—that is to say that the generation step will be rapid), while having a relatively low fusion temperature (about −40° C.), which avoids it for example to freeze when stored outdoor. Moreover, the 1,1'-oxydi-2-propanol (which may be written CH3-HCOH—CH2-O—CH2-HCOH—CH3), dehydrogenated into a dehydrogenated substrate or fraction of the latter (which may be written CH3-CO—CH2-O—CH2-CO—CH3) has a relatively low boiling temperature (about 145° C.), which makes it possible to proceed to a hydrogenation reaction (regeneration step) that is relatively little energy consuming. By comparison, the propylene glycol has a boiling temperature that is not so high (about 188° C.) and its catalytic dehydrogenation is hence not so rapid. Moreover, the propylene glycol does not have two secondary alcohol-type hydroxyl groups easy to dehydrogenate into carbonyl as the dipropylene glycol and in particular the 1,1'-oxydi-2-propanol isomer thereof.

Optionally, the generation step G comprises the dehydrogenation of the hydroxyl groups of the 2,3-butandiol into respective carbonyl groups, in order to generate said dehydrogenated substrate $S_D$ and the gaseous dihydrogen $H_2$, and the regeneration step R further comprises the regeneration of at least a portion of the 2,3-butandiol by hydrogenation of said carbonyl groups into respective hydroxyl groups using gaseous dihydrogen $H_2$. The hydrogen generation module 2 is then optionally designed to dehydrogenate the hydroxyl groups of the 2,3-butandiol into respective carbonyl groups, in order to generate the dehydrogenated substrate $S_D$ and the gaseous dihydrogen $H_2$, and the regeneration module is designed to further regenerate the 2,3-butandiol made by hydrogenation of said carbonyl groups into respective hydroxyl groups using gaseous dihydrogen $H_2$.

According to a particular alternative, the invention also relates to a dihydrogen storage and retrieval method comprising at least:

a step of generating G hydrogen by dehydrogenating hydroxyl groups of a hydrogenated substrate into respective carbonyl groups, in order to generate a dehydrogenated substrate $S_D$ and gaseous dihydrogen $H_2$, and a step of regenerating R the hydrogenated substrate, by hydrogenation of said carbonyl groups into respective hydroxyl groups using gaseous dihydrogen $H_2$, the hydrogenated substrate comprising at least the 1,1'-oxydi-2-propanol and potentially the 2,3-butandiol.

According to this particular alternative, the invention further relates to a dihydrogen storage and retrieval system 1, comprising at least:

- a module for generating hydrogen 2 designed to dehydrogenate hydroxyl groups of a hydrogenated substrate into respective carbonyl groups, in order to generate a dehydrogenated substrate $S_D$ and gaseous dihydrogen $H_2$, and
- a module for regenerating 3 the hydrogenated substrate, designed to hydrogenate said carbonyl groups into respective hydroxyl groups using gaseous dihydrogen $H_2$, the hydrogenated substrate comprising at least the 1,1'-oxydi-2-propanol and potentially the 2,3-butandiol.

The hydrogenated substrate advantageously does not comprise 2,2'-oxydi-1-propanol and/or 2-(2-hydroxy-propoxy)-1-propanol.

Possibility of Industrial Application

To sum up, the invention relates to the problems of storage of dihydrogen, management of renewable energies, including those of intermittent production, and aims in particular to optimize the management of the electricity produced by power plants facing with fluctuating demands of the network, but also to answer to the needs of strategic storage of electric energy (for example, in order to avoid the "blackout", giant power outages or power grid collapse), and to the needs regarding the storage and consumption of dihydrogen taken on board vehicles as a tomorrow's energy carrier.

The invention claimed is:

1. A dihydrogen storage and retrieval method includes at least:

- a step of generating (G) hydrogen by dehydrogenating hydroxyl groups of dipropylene glycol (DG) into respective carbonyl groups in order to generate a dehydrogenated substrate $(S_D)$ and gaseous dihydrogen $(H_2)$; and
- a step of regenerating (R) at least a portion of the dipropylene glycol (DG) by hydrogenating the carbonyl groups into respective hydroxyl groups using the gaseous dihydrogen $(H_2)$.

2. The dihydrogen storage and retrieval method according to claim 1, wherein the hydrogen generation (G) and regeneration (R) steps are carried out using of one or several catalysts.

3. The dihydrogen storage and retrieval method according to claim 1, wherein, during the hydrogen generation step (G), the dehydrogenated substrate $(S_D)$ is in a gaseous state.

4. The dihydrogen storage and retrieval method according to claim 3, wherein, during the hydrogen generation step (G), the dehydrogenated substrate $(S_D)$ and the gaseous dihydrogen $(H_2)$ are evacuated as the dehydrogenation step progresses.

5. The dihydrogen storage and retrieval method according to claim 1, wherein the hydroxyl groups are in a form of a secondary alcohol and the carbonyl groups are in a form of a ketone.

6. The dihydrogen storage and retrieval method according to claim 1, wherein, during the hydrogen generation step (G), two hydroxyl groups of an isomer of the dipropylene glycol (DG) are dehydrogenated into two respective carbonyl groups, and wherein the isomer is 1,1'-oxydi-2-propanol.

7. The dihydrogen storage and retrieval method according to claim 1, wherein, during the hydrogen generation step (G), a hydroxyl group in a form of a secondary alcohol in an isomer of the dipropylene glycol (DG) is hydrogenated into a carbonyl group in a form of a ketone, wherein a hydroxyl group in a form of a primary alcohol in the isomer does not react, and wherein the isomer is 2-(2-hydroxypropoxy)-1-propanol.

8. The dihydrogen storage and retrieval method according to claim 1, wherein, during the hydrogen generation step (G), a 2,2'-oxydi-1-propanol isomer of the dipropylene glycol (DG) does not react.

9. The dihydrogen storage and retrieval method according to claim 1, wherein it comprises, after the hydrogen generation step (G) and before the regeneration step (R), a step of dividing the dehydrogenated substrate $(S_D)$ into several fractions, each of the fractions of the dehydrogenated substrate $(S_D)$ resulting from dehydrogenation or non-dehydrogenation of a different respective isomer of the dipropylene glycol (DG) during the hydrogen generation step (G).

10. The dihydrogen storage and retrieval method according to claim 1, wherein, during the hydrogen generation step (G), all hydroxyl groups of different isomers of the dipropylene glycol (DG), whether in a form of a primary or a secondary alcohol, are dehydrogenated into respective carbonyl groups.

11. The dihydrogen storage and retrieval method according to claim 1, wherein the gaseous dihydrogen $(H_2)$ is produced using renewable energy $(E_r)$.

12. The dihydrogen storage and retrieval method according to claim 1, further comprises a supply step (A) of supplying the gaseous dihydrogen $(H_2)$ to a motor vehicle to ensure propulsion of the motor vehicle.

* * * * *